(12) United States Patent
Bogle et al.

(10) Patent No.: US 8,939,280 B2
(45) Date of Patent: Jan. 27, 2015

(54) SYSTEM AND METHOD FOR DETECTING CONTAMINATION OF A CONVEYOR

(75) Inventors: David W. Bogle, Round Rock, LA (US); Manoj Thomas, Ouderkerk aan de Amstel (NL)

(73) Assignee: Laitram, L.L.C., Harahan, LA (US)

( * ) Notice: Subject to any disclaimer, the term of this patent is extended or adjusted under 35 U.S.C. 154(b) by 5 days.

(21) Appl. No.: 13/823,957

(22) PCT Filed: Sep. 21, 2011

(86) PCT No.: PCT/US2011/052517
§ 371 (c)(1),
(2), (4) Date: Apr. 15, 2013

(87) PCT Pub. No.: WO2012/047515
PCT Pub. Date: Apr. 12, 2012

(65) Prior Publication Data
US 2013/0206545 A1    Aug. 15, 2013

Related U.S. Application Data

(60) Provisional application No. 61/387,212, filed on Sep. 28, 2010.

(51) Int. Cl.
*B65G 17/06* (2006.01)
*B65G 43/00* (2006.01)
*G01N 35/00* (2006.01)

(52) U.S. Cl.
CPC .......... *B65G 43/00* (2013.01); *G01N 35/00009* (2013.01)
USPC .... 198/853; 198/810.01; 198/497; 198/502.1

(58) Field of Classification Search
USPC ............ 198/810.01, 810.02, 810.03, 810.04, 198/850, 853, 502.1, 497
See application file for complete search history.

(56) References Cited

U.S. PATENT DOCUMENTS

| | | | | |
|---|---|---|---|---|
| 3,938,116 | A | * | 2/1976 | Schneider .................. 198/502.1 |
| 4,927,003 | A | * | 5/1990 | Swinderman et al. ........ 198/497 |
| 5,981,268 | A |   | 11/1999 | Kovacs et al. |
| 6,374,990 | B1 | * | 4/2002 | Swinderman ................. 198/497 |
| 6,941,794 | B2 | * | 9/2005 | Strohmeyer et al. ......... 73/28.01 |
| 6,993,405 | B2 | * | 1/2006 | Beaulieu et al. .............. 700/116 |
| 7,232,036 | B2 | * | 6/2007 | Van Slyke et al. ............. 210/526 |
| 7,494,004 | B2 | * | 2/2009 | Stolyar et al. ............ 198/810.02 |
| 7,635,060 | B2 | * | 12/2009 | Lagneaux ............... 198/810.04 |
| 7,673,740 | B2 | * | 3/2010 | Kusel ....................... 198/810.02 |
| 7,964,144 | B1 | * | 6/2011 | Nordin et al. ................. 422/68.1 |
| 8,346,482 | B2 | * | 1/2013 | Fernandez ...................... 702/19 |

(Continued)

OTHER PUBLICATIONS

Joe Dirksen, "Monitoring and Controlling Microbial Contamination in the Beer Filling Area," MBAA Technical Quarterly, vol. 42, No. 1, 2005, pp. 34-44, Master Brewers Association of America, St. Paul, MN.

*Primary Examiner* — Leslie A Nicholson, III
*Assistant Examiner* — Keith R Campbell
(74) *Attorney, Agent, or Firm* — James T. Cronvich

(57) ABSTRACT

Conveying systems and method for detecting the presence and amount of biological contaminants or additives on a conveyor belt. The conveyor system includes a conveyor belt having embedded biosensors. Transmitters co-located in the belt with the biosensors transmit biosensor signals to a remote controller. The remote controller allows remote monitoring of the contamination level on the conveyor belt.

19 Claims, 4 Drawing Sheets

(56) References Cited

U.S. PATENT DOCUMENTS

| | | | |
|---|---|---|---|
| 8,397,904 B2 * | 3/2013 | Bogle | 198/810.04 |
| 2005/0043894 A1 | 2/2005 | Fernandez | |
| 2007/0039877 A1 | 2/2007 | Van Slyke et al. | |
| 2008/0060910 A1 * | 3/2008 | Younkin et al. | 198/348 |
| 2008/0133051 A1 | 6/2008 | Wallace et al. | |

* cited by examiner

SYSTEM AND METHOD FOR DETECTING CONTAMINATION OF A CONVEYOR

BACKGROUND

The invention relates generally to power-driven conveyors conveying articles and more particularly to conveyor belts with embedded biosensors and methods of detecting biological contaminants or additives on conveyor belts.

Biological contamination or improper levels of additives can compromise the quality and safety of food products. In many applications, food products are conveyed through continuous processes on a conveyor belt. Typical methods of detecting the presence of biological contaminants or additives on food products include the steps of taking samples of the food products or of food fluids, rinse water, or other specimens that come in contact with the food products, culturing those samples in a Petri dish, and observing the culture under a microscope. Those steps rely to a great degree on human participation and can be time-consuming.

SUMMARY

These shortcomings are overcome by a conveying belt embodying features of the invention. One version of such a conveyor belt comprises a biosensor that advances along a conveyor path with the conveyor belt, senses the presence of a predetermined analyte, and produces a corresponding response signal.

In another aspect of the invention, a conveying system embodying features of the invention comprises a conveyor belt that includes a biosensor sensing the presence of a predetermined analyte and producing a corresponding response signal and a transmitter transmitting the response signal. A receiver remote from the conveyor belt receives the response signal transmitted by the transmitter.

Another version of a conveying system embodying features of the invention comprises a conveyor belt that includes a biosensor sensing the presence of a predetermined analyte and a biosensor-loading-unloading device for loading and unloading the biosensor in the conveyor belt.

Yet another version of a conveying system embodying features of the invention comprises a conveyor belt having an outer surface atop which articles are conveyed along a carryway. A scraper has a scraping end that contacts the outer surface of the conveyor belt off the carryway to scrape residue from the outer surface. A collector is positioned to receive the residue scraped from the outer surface of the conveyor belt by the scraper. A biosensor disposed in the collector senses the presence of a predetermined analyte and produces a corresponding response signal.

In another aspect of the invention, a method for monitoring a process for contamination of articles conveyed continuously through the process on a conveyor belt comprises: (a) advancing articles supported on a conveyor belt along a conveyor path; (b) detecting a predetermined analyte at an outer surface of the conveyor belt with a biosensor mounted in and advancing with the conveyor belt and producing measurements; and (c) transmitting the measurements remotely from the conveyor belt to a monitoring station.

BRIEF DESCRIPTION OF THE DRAWINGS

These aspects and features of the invention are better understood by referring to the following description, appended claims, and accompanying drawings, in which:

DETAILED DESCRIPTION

Figure 1:
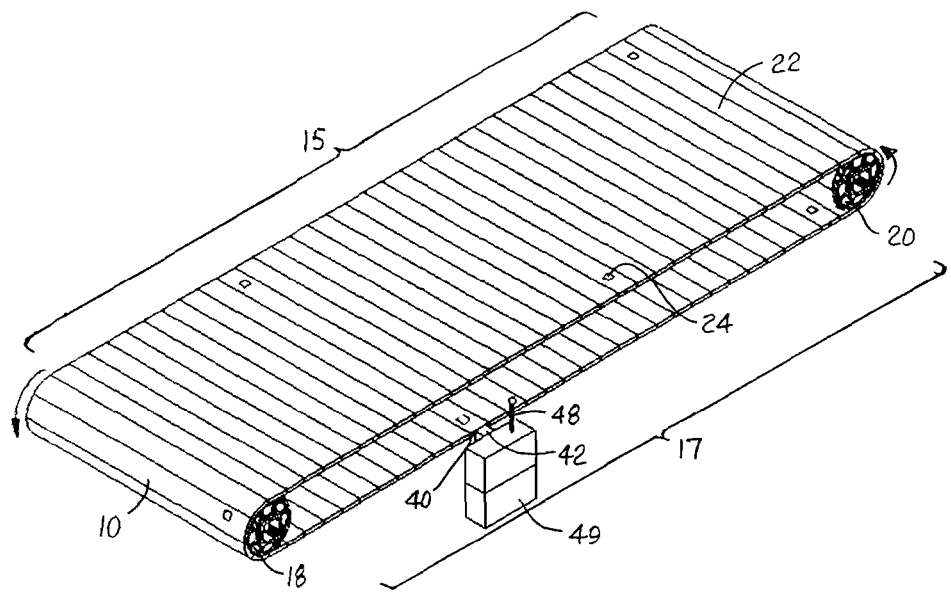
FIG. 1 is an isometric view of a conveyor system embodying features of the invention including a conveyor belt with biosensors.

One version of a conveyor system embodying features of the invention is shown in FIG. 1. A conveyor, shown in this example as a conveyor belt 10, carries articles 12 on an outer surface 22 along a carryway segment 15 of the belt's endless conveyor path. For example, the conveyor belt 10 may carry articles such as vegetables, fruits, poultry, meat, fish or other raw or processed foodstuffs along the carryway 15. At the end of the carryway, the articles are conveyed off the conveyor belt. After rounding drive sprockets 18, the conveyor belt 10 follows a return segment 17 on its way back around idle sprockets 20 to the carryway segment 15.

One or more biosensors 24 disposed in or on the belt 10 are set to detect one or more analytes that may be contaminating or degrading the articles and to provide a response to the presence of a predetermined analyte. In this example, which shows a modular plastic conveyor belt constructed of rows of hinged modules, the biosensors are shown at spaced apart locations along the length of the belt and across its width. The sensors open onto the belt's outer surface 22 on which fluids, fats, and other specimens from the articles that could contain contaminants or additives would reside. Examples of analytes present in the specimens that may be selectively sensed by the biosensors include: pathogenic microorganisms, contaminants, additives, degradation products, chemical markers of microbial infestation, bacteria, bacterial endotoxins, mycotoxins, botulism, food poisoning, *streptococcus*, *E. coli.*, *salmonella*, cholera, protozoan pathogens, *staphylococcus*, viruses, and fungi.

Figure 2:
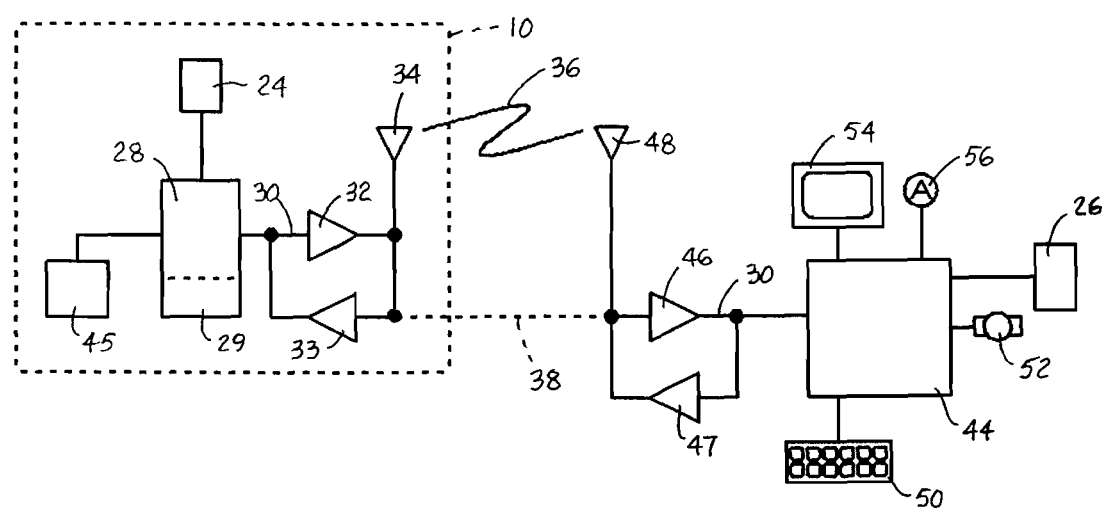
FIG. 2 is a block diagram of the conveyor system of FIG. 1.

As shown in FIG. 2, each biosensor is connected to a logic circuit 28 in the conveyor belt 10. Each logic circuit may be realized by a programmed microcontroller or by hardwired logic elements. Conventional signal-conditioning circuit components, such as buffers, amplifiers, analog-to-digital converters, and multiplexers, may be interposed between the biosensors and the logic circuit. The logic circuit may also include a unique address or other identifying indicia to correlate the response of each biosensor with a specific sensor position on the conveyor belt. The identifying indicia and the biosensor response may be stored in one or more memory elements 29. The biosensor, which may include an integral or an external transducer, produces a response that is converted into a biosensor signal 30 that is transmitted remotely by a transmitter 32. The transmitter may be a wireless RF transmitter transmitting wirelessly via an antenna 34 over a wireless communication link 36 or over an ohmic connection 38 between a conductive contact 40 on the outside of the belt 10 and a brush 42 in conveyor structure along the side of the belt, as in FIG. 1. A receiver 33 may also be connected to the logic circuit to receive command and control signals from a remote controller 44, i.e., a controller not located on or in the conveyor belt. Other transmitter-receiver technologies, such as optical or infrared, for example, may be used. All the components embedded in the belt may be powered by a power source 45, such as one or more battery cells, housed together in a cavity in the belt. Alternatively, the power source 45 may be an energy harvester harvesting energy from vibratory motion or articulation of the conveyor, thermal gradients, or other energy-producing effects inherent in the process or conveyance. The embedded power source 45 may alternatively be powered by induction or by RF charging as it recirculates past an external charging device 49, as in FIG. 1.

A remote receiver 46 receives the biosensor signal 30 via an antenna 48 over the wireless communication link 36 or over the ohmic connection 38 from the receiver 33 embedded in the conveyor belt. The receiver 46 sends the biosensor signal to the remote controller 44. A transmitter 47 connected between the controller 44 and the antenna 48 or the ohmic connection 38 may be used to send command and control signals to the belt-borne biosensor circuits. An operator input device 50 connected to the controller 44 may be used to select biosensor or alarm settings or displayed data. From the settings and the biosensor response to, for example, the level of a certain additive, the controller adjusts an additive supplier 26 to correct the level of the additive to within an optimum range. The controller 44 may also be used to control the speed of the motor 52 driving the drive sprockets or to stop the conveyor. A video display 54 may be used to monitor system operating conditions and settings or display alarm conditions. A more clearly visible or audible alarm 56 may also be used by the controller to warn of irregularities in the process, such as the amount of analyte exceeding a predetermined level. The controller may be a programmable logic controller, a laptop, a desktop, or any appropriate computer device.

Figure 3A:
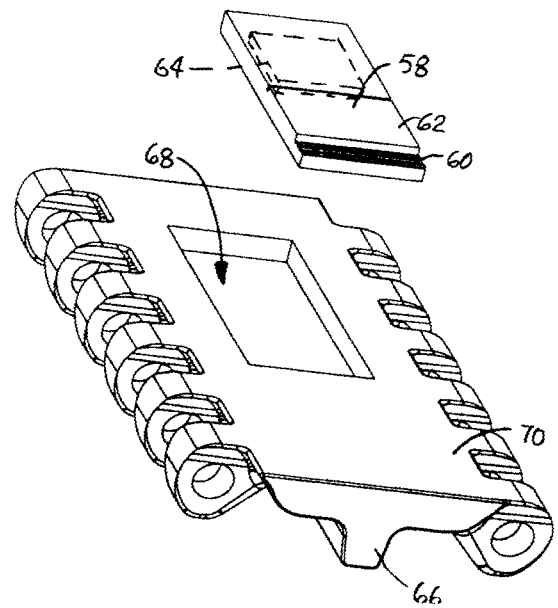
FIGS. 3A and 3B are axonometric views of a conveyor belt module with an embedded biosensor usable in a conveyor belt as in FIG. 1 showing the biosensor before and after installation.
Figure 3B:
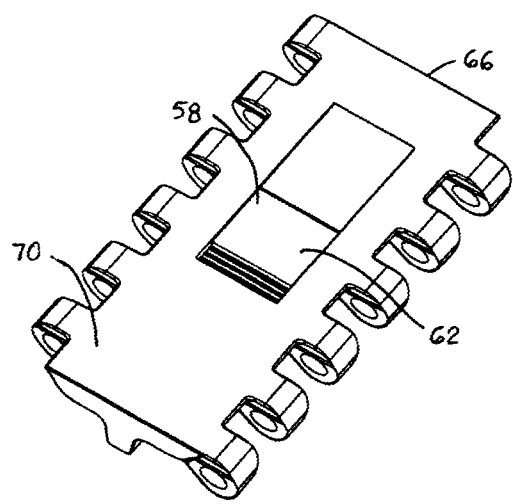

One version of a biosensor is a microelectromechanical (MEMS)-based impedance biosensor 58 in chip form as shown in FIGS. 3A and 3B. The MEMS-based biosensor comprises a silicon chip with interdigitated electrodes in the form of parallel rows of electrodes 60 and an exterior sensing surface 62. When a predetermined analyte, such as *E. coli* O157:H7 bacteria, binds to the sensing surface, the impedance between the electrodes changes with the concentration level of the analyte. When the sensor applies a known voltage across the electrodes, the change in impedance is measured as a change in current, which is the biosensor's response to the presence of the predetermined analyte (in this example, *E. coli*.). The signal-conditioning circuitry in the biosensor converts the response into the biosensor signal 30 that is transmitted off the belt and compared to an impedance-level setting by the remote controller 44 (FIG. 2) to determine the concentration of analyte and sound the alarm 56, stop the conveyor belt 10, adjust the injection of additives, or take whatever course of action had been prescribed. The signal-conditioning circuitry, logic circuitry, transmitter, antenna, and other related components composing the biosensor's support circuitry 64 are co-located with the biosensor 58. A sensing belt module 66 having a cavity 68 opening onto a top surface 70 of the module holds the biosensor 58 with its sensing surface 62 flush with the top surface 70 of the module. The sensing belt module may be connected side to side with other sensing modules or with standard modules without sensors to form belt rows and the rows connected hingedly end to end to realize the conveyor belt 10 of FIG. 1 as a modular conveyor belt. The belt modules are made, for example, of a thermoplastic polymer material in an injection-molding process. The biosensor 58 can be retained in the cavity 68 by adhesives or by mechanical means, such as snap-lock retention structure, lids or other retainers affixable to the module, or by suction cups.

Figure 4:
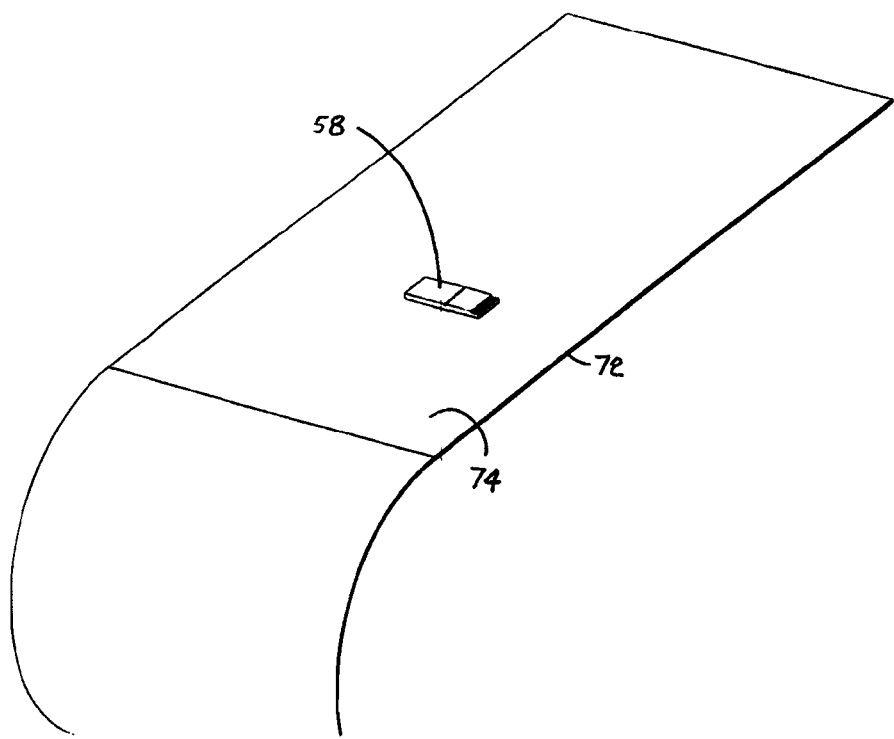
FIG. 4 is an isometric view of a portion of a flat belt with an attached biosensor usable in a conveyor system as in FIG. 1.

The conveyor belt in FIG. 1 is alternatively realized as a flat belt 72, with or without drive elements on the inner side, as in FIG. 4. In this version of conveyor belt, the biosensors 58 are affixed to the outer surface 74 of the belt by bolts, screws, rivets, adhesives, or other fasteners. But the biosensors or their support circuits could alternatively be molded or extruded into the belt during manufacture.

Figure 5A:
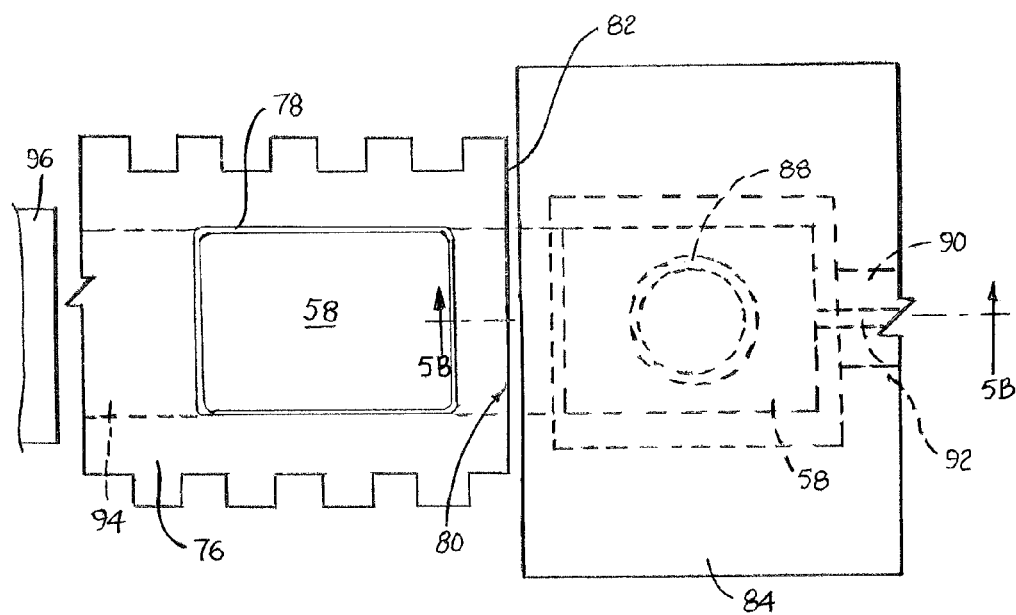
FIG. 5A is top plan view of a biosensor-loading-unloading device usable with a conveyor system as in FIG. 1.
Figure 5B:
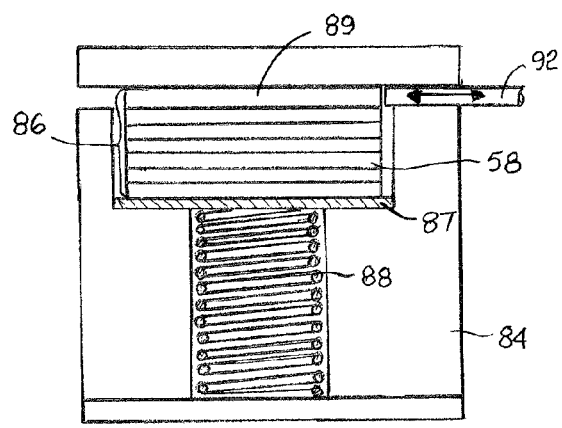
FIG. 5B is a cross-sectional view of the biosensor-loading-unloading device viewed along 5B-5B of FIG. 5A.

FIGS. 5A and 5B show a belt sensor module 76 similar to the module 66 shown in FIGS. 3A and 3B. A cavity 78 for the biosensor has an opening 80 onto an outer side 82 of the module 76. Adjacent to the outer side 82 of the belt module is a biosensor-loading-unloading device 84, which houses a stack 86 of biosensors 58. A coil spring 88 biases the stack 86 of biosensors 58 resting on a spring plate 87 upward toward a loading position 89, from which the biosensor 58 can be automatically loaded into the cavity 78 in the belt module. A pneumatic actuator 90 with a pushing member, or push rod 92, pushes the biosensor 58 at the top of the stack into the cavity 78 through the opening 80 in the outer side 82 of the module 76. Other linear actuators, such as hydraulic, electromagnetic, or electromechanical, may be used instead to load the biosensor into the sensing position. The controller 44 (FIG. 2) can control the actuator to load biosensors according to a predetermined set schedule. The sensing module 76 and any other belt modules across the belt row may also have lateral passageways 94 communicating with the cavity 78. With an elongated pushing member, the actuator 90 can be used unload the biosensor by pushing it from the cavity through the laterally aligned passageways and out the opposite side of the belt into a drop box 96 for collection. Thus, the loading and unloading of biosensors can be easily coordinated by using the same actuator to move the biosensors into or out of the conveyor belt. Of course, the actuator can be used for loading the biosensor into the cavity with unloading performed manually or by some other means.

Figure 6:
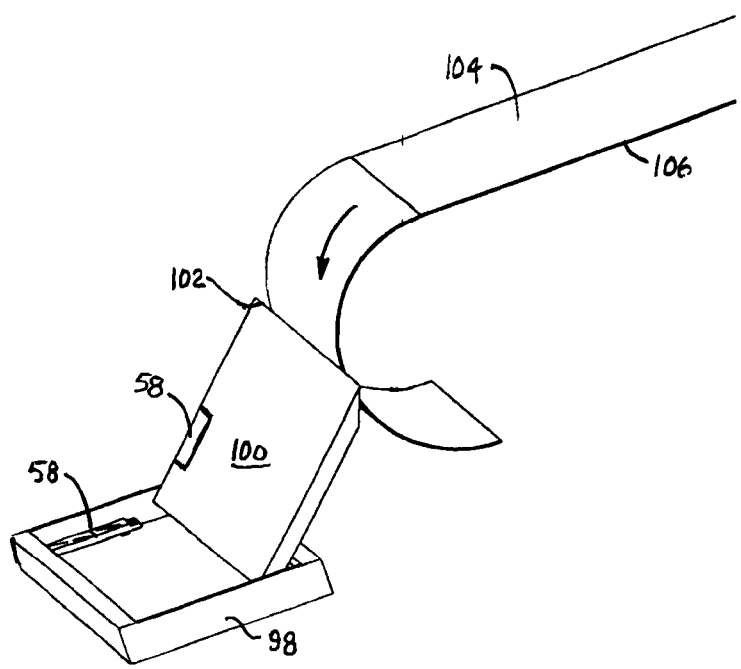
FIG. 6 is an isometric view of another version of a conveyor system embodying features of the invention including a biosensor disposed in a tray in which residue scraped from a conveyor belt is collected.

As shown in FIG. 6, a biosensor 58 is disposed in a collector 98, such as a tray. A scraper 100, which has a scraping end 102, or blade, contacting the outer surface 104 of a conveyor belt 106 as it wraps around a sprocket or pulley set (not shown). Residue on the conveyor belt 106 is scraped from the outer surface 104 by the scraper 100 and directed into the collector tray 98. The biosensor 58 detects the presence and amount of a predetermined analyte in the residue scraped from the conveyor belt. Alternatively, the biosensor 58 can be embedded in the scraper 100.

Although the invention has been described in detail with respect to a preferred version, other versions are possible. For example, the sensing portion of the biosensor could be housed in a separate carrier from the support circuitry so that the biosensor can be replaced without replacing the rest of the circuitry. The rest of the circuitry can be made a permanent part of the belt by integrally molding or extruding it with the belt or by potting it in a belt cavity. As another example, the biosensors depicted in the examples are shown with their sensing surfaces at left and right sides of the belts. But they could be positioned anywhere across the width of the belts, in the underside of the belt, or in the hinge area of the modular belts depending on the best position to encounter the specimens. The remote controller provides the flexibility to take many kinds of actions in response to an excessive amount of analyte. Besides those actions mentioned, the controller could: schedule later production runs for more frequent testing; sound different levels of alarms depending on the severity of the contamination; initiate remedial or prophylactic actions, such as sanitizing, dumping, and reprocessing, in the process; provide more remote monitoring of the process via Internet, cell system, or satellite relay; or send remote alarms via various alert systems, such as text messaging, email, or pager signal. So, as these few examples suggest, the scope of the claims is not meant to be limited to the details of the example versions used to describe features of the invention.

What is claimed is:

1. A conveyor belt comprising a biosensor advancing along a conveyor path with the conveyor belt and sensing the presence of a predetermined analyte and producing a corresponding response signal, and further comprising an opening in an outer side of the conveyor belt through which replacement biosensors are loaded to replace spent biosensors.

2. A conveyor belt as in claim 1 further comprising a transmitter associated with the biosensor, the transmitter transmitting the response signal.

3. A conveyor belt as in claim 1 wherein the biosensor is a MEMS-based sensor.

4. A conveyor belt as in claim 3 wherein the MEMS-based sensor has an exterior sensing surface whose impedance changes with the amount of predetermined analyte on the exterior sensing surface and wherein the response signal indicates the change in impedance.

5. A conveyor belt as in claim 1 further comprising a cavity in the conveyor belt and wherein the biosensor resides in the cavity.

6. A conveyor belt as in claim 1 wherein the biosensor is affixed to an outer surface of the conveyor belt.

7. A conveyor system as in claim 1, further comprising:
a scraper having a scraping end that contacts the outer surface of the conveyor belt off the carryway to scrape residue from the outer surface;
a collector positioned to receive the residue scraped from the outer surface of the conveyor belt by the scraper; and
a second biosensor disposed in one of the scraper and the collector to sense the presence of a predetermined analyte and produce a corresponding response signal.

8. A conveyor system as in claim 7 wherein the second biosensor is a MEMS-based sensor.

9. A conveyor system as in claim 8 wherein the MEMS-based second biosensor has an exterior sensing surface whose impedance changes with the amount of predetermined analyte on the exterior sensing surface and wherein the response signal indicates the change in impedance.

10. A conveyor system as in claim 7 wherein the second biosensor includes a transmitter transmitting the response signal and the conveyor system further includes a receiver remote from the second biosensor receiving the response signal transmitted by the transmitter.

11. A conveyor system comprising:
a conveyor belt including:
a biosensor sensing the presence of a predetermined analyte and producing a corresponding response signal;
a transmitter transmitting the response signal;
a receiver remote from the conveyor belt receiving the response signal transmitted by the transmitter;
a biosensor-loading-unloading device for loading and unloading the biosensor in the conveyor belt.

12. A conveyor system as in claim 11 wherein the biosensor is a MEMS-based sensor having an exterior sensing surface whose impedance changes with the amount of predetermined analyte on the exterior sensing surface and wherein the response signal indicates the change in impedance.

13. A conveyor system as in claim 11 wherein the biosensor is affixed to an outer surface of the conveyor belt.

14. A conveyor system as in claim 11 further comprising a remote station external to the conveyor belt, the remote station processing the response signal received by the receiver to monitor the biosensor.

15. A method for monitoring a process for contamination of articles conveyed continuously through the process on a conveyor belt, comprising:
advancing articles supported on a conveyor belt along a conveyor path;
detecting a predetermined analyte at an outer surface of the conveyor belt with a biosensor mounted in and advancing with the conveyor belt and producing measurements;
transmitting the measurements remotely from the conveyor belt to a monitoring station;
replacing spent biosensors with replacement biosensors through an opening in an outer side of the conveyor belt.

16. The method of claim 15 further comprising actuating an alarm if the measurements exceed a predetermined limit.

17. A conveyor system comprising: a conveyor belt including a biosensor advancing along a conveyor path with the conveyor belt and sensing the presence of a predetermined analyte and producing a corresponding response signal;
a biosensor-loading-unloading device for loading and unloading the biosensor in the conveyor belt.

18. A conveyor system as in claim 17 wherein the conveyor belt includes a cavity housing the biosensor and an opening from the cavity onto an outer side of the conveyor belt and wherein the biosensor-loading-unloading device includes a pushing member that pushes the biosensor into the cavity through the opening in the outer side of the conveyor belt.

19. A conveyor system as in claim 17 wherein the conveyor belt includes a cavity housing the biosensor and a lateral passageway in communication with the cavity and opening onto an outer side of the conveyor belt and wherein the biosensor-loading-unloading device includes a pushing member that pushes the biosensor from the cavity through the lateral passageway and the outer side of the conveyor belt.

* * * * *